United States Patent
Mazda et al.

(10) Patent No.: US 7,166,108 B2
(45) Date of Patent: Jan. 23, 2007

(54) DEVICE FOR FIXING A ROD AND A SPHERICAL SYMMETRY SCREW HEAD

(75) Inventors: Keyvan Mazda, Paris (FR); Régis Le Couedic, Bordeaux (FR)

(73) Assignee: Abbott Spine, Bordeaux (FR)

( * ) Notice: Subject to any disclaimer, the term of this patent is extended or adjusted under 35 U.S.C. 154(b) by 602 days.

(21) Appl. No.: 10/433,371

(22) PCT Filed: Dec. 7, 2001

(86) PCT No.: PCT/FR01/03870

§ 371 (c)(1),
(2), (4) Date: Jun. 3, 2003

(87) PCT Pub. No.: WO02/45607

PCT Pub. Date: Jun. 13, 2002

(65) Prior Publication Data
US 2004/0039385 A1   Feb. 26, 2004

(30) Foreign Application Priority Data
Dec. 7, 2000 (FR) .................................. 00 15868
May 18, 2001 (FR) .................................. 01 06557

(51) Int. Cl.
*A61B 17/56* (2006.01)
(52) U.S. Cl. ........................................................ 606/61
(58) Field of Classification Search ............ 606/60–61, 606/69–73
See application file for complete search history.

(56) References Cited

U.S. PATENT DOCUMENTS

| 3,253,843 | A |   | 5/1966 | Statham | |
|---|---|---|---|---|---|
| 4,653,481 | A | * | 3/1987 | Howland et al. | 606/61 |
| 4,719,905 | A | * | 1/1988 | Steffee | 606/61 |
| 5,133,717 | A | * | 7/1992 | Chopin | 606/61 |
| 5,306,275 | A | * | 4/1994 | Bryan | 606/61 |
| 5,312,404 | A | * | 5/1994 | Asher et al. | 606/61 |
| 5,330,473 | A | * | 7/1994 | Howland | 606/61 |
| 5,344,422 | A | * | 9/1994 | Frigg | 606/61 |
| 5,437,670 | A |   | 8/1995 | Sherman et al. | |

(Continued)

FOREIGN PATENT DOCUMENTS

EP      0 933 065 A      8/1999

(Continued)

*Primary Examiner*—Eduardo C. Robert
*Assistant Examiner*—Annette R Reimers
(74) *Attorney, Agent, or Firm*—Dennis G. LaPointe

(57) ABSTRACT

A fixing device adapted to connect a rod and a nearby spherically symmetrical screwhead, including a first longitudinal member (14) having a first surface (16) and a second surface (20), a first end (18) of said first surface (16) being adapted to be pressed against said screwhead (10) and a middle part (22) of said second surface (20) being adapted to bear against a portion of said rod (12), and a second longitudinal member (15) adapted to co-operate with said first longitudinal member (14), whose first end (35) is adapted to be pressed, opposite a portion of said first end (18) of said first surface (16) of said first part (14), against a second hemispherical part (38) of said screwhead (10) opposite the first (29) and whose middle portion (36) is adapted to bear against a portion (34) of a second part of said rod (12) opposite the first part.

13 Claims, 5 Drawing Sheets

U.S. PATENT DOCUMENTS

| | | | | |
|---|---|---|---|---|
| 5,527,310 A | * | 6/1996 | Cole et al. | 606/60 |
| 5,584,831 A | | 12/1996 | McKay | |
| 5,702,395 A | * | 12/1997 | Hopf | 606/61 |
| 6,749,612 B1 | * | 6/2004 | Conchy et al. | 606/61 |

FOREIGN PATENT DOCUMENTS

| | | |
|---|---|---|
| FR | 2727620 A | 6/1996 |
| FR | 2784282 A | 4/2000 |
| WO | WO 0028907 A | 5/2000 |

* cited by examiner

DEVICE FOR FIXING A ROD AND A SPHERICAL SYMMETRY SCREW HEAD

FIELD OF INVENTION

The present invention relates to a fixing device for connecting a rod and a nearby screw head with spherical symmetry.

One particular field of application that is envisaged is that of spinal column surgery and more particularly that of stabilizing the spine to alleviate certain problems connected with traumas or degenerative pathologies.

Stabilizing devices including pedicular screws and a connecting rod which interconnects the heads of said screws are well-known in the art. The pedicular screws of these devices generally have a U-shaped receiving head adapted to receive the rod, and the inside wall of the head is threaded coaxially with said screw to enable an immobilizing part to be screwed against said rod. Thus the rod is fastened to said screw because it is directly clamped to it by the immobilizing part, which, in conjunction with the bottom of the receiving head, forms a vice.

However, the connecting force between a receiving head and the rod passing through it is determined by the clamping force transmitted to the immobilizing part.

This immobilizing force is directly related to the physical strength of the operator, which is likely to vary from person to person.

What is more, in these devices, the screw and the connecting rod are connected together and their relative directions are determined by the shape of the receiving head.

BACKGROUND OF THE INVENTION

To remedy this drawback, a U-shaped receiving head has been designed having a spherically symmetrical outside surface and into which a threaded connecting rod is inserted so that two nuts can be screwed to opposite sides of the head, forming a vice that holds the pedicular screw and the connecting rod in a fixed position. Because the screwhead is spherically symmetrical, the rod can be oriented in different positions relative to the screw; its positions relative to the screw are restricted to the plane of symmetry between the two branches of the U-shaped screwhead and containing the body of the screw.

Furthermore, the two nuts forming the vice also have the clamping force drawback, because the nuts are screwed directly against the receiving head.

An object of the present invention is to remedy those drawbacks by proposing a fixing device with which the clamping force is increased.

This object is achieved by virtue of the fact that the device includes a first longitudinal member having a first surface and an opposite second surface, a first end of said first surface being adapted to be pressed against a portion of a first hemispherical part of said screwhead and a middle part of said second surface being adapted to bear against a portion of a first part of said rod, a second longitudinal member adapted to co-operate with said first longitudinal member, whose first end is adapted to be pressed, opposite a portion of said first end of said first surface of said first member, against a portion of a second hemispherical part of said screwhead opposite the first hemispherical part and whose middle part is adapted to bear against a portion of a second part of said rod opposite the first, and first fastening and adjustment means adapted to hold the second ends of said first and second longitudinal members facing each other and to move them toward each other so as to cause said second longitudinal member to pivot around said rod relative to said first longitudinal member to grip said screwhead between said first end of said first surface and simultaneously to grip said first end of said second longitudinal member and said rod between said middle part of said second surface of said first longitudinal member and the middle part of said second longitudinal member, whereby said device connects said rod and said screwhead and holds them in a fixed position relative to each other.

Thus one feature of the fixing device is the method of immobilizing and clamping the receiving head and the rod by pivoting two longitudinal members relative to each other about the rod so that the first ends of said longitudinal members form a first clamp adapted to grip the spherically symmetrical screwhead and their middle parts form a second clamp adapted to grip the rod simultaneously. The two longitudinal members pivot about the rod by virtue of the first fastening and adjustment means, which enable the second ends of said longitudinal members to be moved forcibly toward each other. In this way, through a lever effect, the force applied to move the second ends toward each other enables the first ends of the longitudinal members to form a vice and to grip the screwhead and the rod simultaneously with a force much greater than that obtained by clamping an immobilizing part directly against the rod.

Furthermore, because the rod is gripped near the spherically symmetrical screwhead, the screwhead has no notch, into which the rod would otherwise have to be inserted, and therefore forms a true ball-and-socket joint, so that the positions of the rod relative to the pedicular screw are no longer limited to one plane.

In a preferred embodiment, the first end of said first surface forms a spherical socket whose bottom includes a bore opening onto the end of the second surface of said longitudinal member, said spherical socket being adapted to be pressed onto said screwhead. Thus the first end is locked perfectly against the screwhead because the end of the surface mates perfectly with the surface of the screwhead. Furthermore, the bore that is formed in the part at the bottom of the spherical socket provides access to the top of the screwhead, which has a hexagonal housing for screwing in the pedicular screw. Thus the screw can be screwed tightly into the vertebra even if the fixing device is already mounted on the screwhead.

The middle part of said second surface advantageously includes a first housing in which said portion of a first part of said rod is adapted to bear. Thus the rod is prevented from moving in translation in the direction of the first longitudinal member, which improves the immobilization of the rod relative to the head.

In one particularly advantageous embodiment, the second longitudinal member has a portion facing said second surface of said first longitudinal member and a curved portion forming said first end of the said second longitudinal member. The second longitudinal member, bearing on the rod, is therefore able to pivot around the rod within the limits of contact with the first longitudinal member. When the first longitudinal member is bearing against a hemispherical first part of the screwhead, the curved portion of said longitudinal member is pressed against the second hemispherical portion of the screwhead to grip it.

The first end of said second longitudinal member advantageously has a truncated spherical socket portion adapted to be pressed against said portion of the second hemispherical part of said screwhead. Accordingly, the shape of the end of said second longitudinal member coincides perfectly with the surface of the screwhead, which improves fastening.

Said portion facing said second surface of said first longitudinal member preferably has a bore opening opposite said bore opening onto the end of the second surface of said longitudinal member, through which said screwhead is accessible when said device is mounted.

In one particular embodiment, the middle part of said second longitudinal member includes a second housing adapted to receive said rod and situated opposite said first housing. Thus said rod is also immobilized against movement in translation parallel to said second longitudinal member. The rod can therefore be gripped between the two longitudinal members.

The first fastening and adjustment means advantageously include a screw adapted to pass through said second ends of said first and second longitudinal members, whose head is pressed against said end of said second longitudinal member and whose body is screwed into an internal screwthread in the second end of said first longitudinal member. Accordingly, tightening the screw tends to move the second ends of the longitudinal members toward each other and to hold them together, their middle portions respectively bearing, in order to form pivots, against a portion of a first part of said rod and against a portion of a second part of said rod opposite the first part, so that the first ends of said longitudinal members grip the screwhead to immobilize the assembly.

In a first particular embodiment, the invention is applied to a spine stabilizing system including two spherical head pedicular screws each adapted to be screwed into a pedicle of a vertebra, two fixing devices according to the invention mounted on said screwheads with said longitudinal members substantially parallel to each other and to the axis of the spine, a transverse rod substantially perpendicular to the axis of the spine adapted to join said two devices together, and a connecting system adapted to connect said transverse rod to a longitudinal rod substantially parallel to the axis of the spine.

Thus this first particular embodiment of the stabilizing system holds the vertebrae of a portion of the spine together when the anatomical members adapted to provide this function are missing. To this end, the fixing devices according to the invention mounted on each of the two pedicular screws fixed into a vertebra are joined together by a transverse rod forming a rung on the vertebra, and the rungs are joined together by longitudinal rods by means of a connecting system adapted to fasten together two substantially perpendicular rods.

In a second particular embodiment, the invention is applied to a spine stabilizing system including two spherical head pedicular screws adapted to be screwed into the pedicles of two superposed vertebrae, two fixing devices according to the invention mounted on said two screwheads with said longitudinal members substantially parallel to each other and perpendicular to the axis of the spine, and a longitudinal rod substantially parallel to the axis of the spine adapted to connect said devices together.

Accordingly, the devices according to the invention are mounted on two pedicular screws fixed into two successive vertebrae, on the same side of the spine, and are joined together by a rod so as to hold the two facing pedicles of two successive vertebrae in a fixed position. To reinforce the spinal column symmetrically, a similar system is fitted on the other side of the spine.

In a third particular embodiment, the invention is applied to a spine stabilizing system including at least two spherical head pedicular screws each adapted to be screwed into a pedicle of a vertebra, two devices according to the invention mounted on said screwheads with said second ends of said longitudinal members directed towards each other, and a transverse connecting part fastened to a second end of said parts of said two devices and adapted to connect said two devices together.

Just as in the preceding particular embodiment, the fixing device according to the invention connects superposed pedicular screws with rods disposed parallel to the axis of the spine. However, in this third embodiment, the devices are connected together, transversely from one side of the spine to the other, by a transverse connecting part.

In a fourth particular embodiment of the invention, the fixing device further includes second adjustable fastening means fastened to said second longitudinal member and situated between its first end and its middle part, and said second fastening means are adapted to bear against the first end of said second surface of said first longitudinal member so as to move said first end of said second longitudinal member and said portion of said first end of said first surface of said first member toward each other to trap said screwhead, whereby said longitudinal members are adapted to pivot relative to each other about said spherically symmetrical screwhead between a position in which said second ends of said longitudinal members are spaced apart from each other and a position in which said second ends of said longitudinal members are close to each other.

Accordingly, apart from the fact that it improves the immobilization of the spherically symmetrical screwhead, this feature also fastens the first ends of the longitudinal members together in a non-demountable fashion, without said second ends of said first and second longitudinal members having to be connected by said first fastening and adjustment means. The rod therefore be adjusted relative to the two longitudinal members, which remain fastened to the spherical symmetrical screwhead before they are immobilized by moving said second ends of said second longitudinal members toward each other by means of the first fastening means.

Said second fastening means advantageously consist of a screwthreaded member adapted to co-operate with an internal screwthread formed in the wall of said first bore, said screwthreaded member being adapted to bear against the first end of said second surface of said first longitudinal member. Accordingly, rotation of said screwthreaded member entrains it in translation in the direction of the first end of said second surface of said first part, or in the opposite direction.

Said second end of said second longitudinal member preferably has a U-shaped recess opening in the direction away from said first end, said screw passing in an inclined manner through said second end of said first longitudinal member so that said screwhead is spaced apart from said first end when it is unscrewed and close to said first end when it is screwed in, whereby said screw is adapted to be engaged in said U-shaped recess, with said screwhead bearing against the perimeter of said recess.

Thus, by virtue of this feature, the second longitudinal member can be pivoted around the screwhead, moving said second ends away from each other, when said second adjustable fastening means are operated, with the screw remaining in an unscrewed position in said first longitudinal member, in which unscrewed position the screwhead is remote from the first end. Thus the screw can be inserted before mounting the device and then tightened to immobilize said rod, as explained in more detail later in the description.

It is particularly advantageous if said first longitudinal member further includes a second bore situated between said middle part and second end of said first longitudinal member, opening onto said first and second surfaces, respectively, and adapted to receive a screw whose head is pressed against said second surface to hold said first longitudinal member in a fixed position relative to a wall with said first surface against said wall. In the fourth embodiment of the invention, this particular feature enables said fixing device to be connected to the lateral walls of the vertebral bodies.

The fourth embodiment of a device according to the invention is advantageously applied to a spine stabilizing system which includes two fixing devices according to the invention and two spherical head posterior screws each adapted to be screwed into the posterior lateral wall of the vertebral body of a respective one of two superposed vertebrae, in which system said first longitudinal members are adapted to be held in a fixed position relative to each other, substantially parallel to each other and to the median planes of said vertebrae, and against the lateral wall of the vertebrae by anterior screws passing through said second bore, the first ends of the first surfaces respectively bearing against said spherical heads, and the two fixing devices being held in a fixed position relative to each other by a single rod gripped by the median parts of respective longitudinal members. Thus the two vertebrae are held relative to each other, so that in particular said assembly partly supplants the intervertebral disc.

BRIEF DESCRIPTION OF THE DRAWINGS

Other features and advantages of the invention will emerge on reading the following description of particular embodiments of the invention, which description is given by way of non-limiting example and with reference to the accompanying drawings, in which.

DETAILED DESCRIPTION

Figure 1:
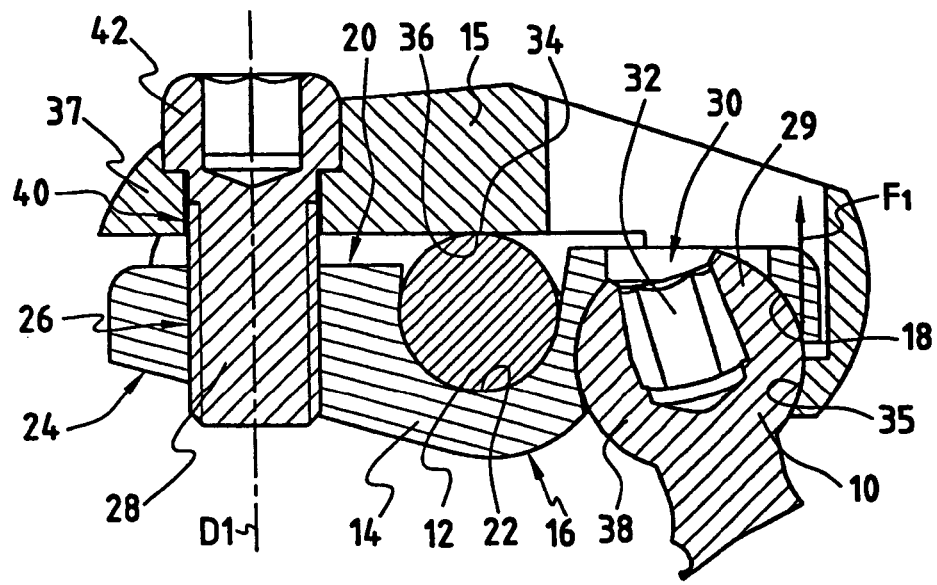
FIG. 1 is a diagrammatic view in vertical section of a fixing device according to the invention connecting a rod (seen in perpendicular section) and a spherically symmetrical head.

A fixing device according to the invention and how it works are described first with reference to FIG. 1.

The fixing device according to the invention holds a spherically symmetrical screwhead 10 and a rod 12 together in a particular relative position in which they are situated near each other. The device includes a first longitudinal member 14 and a second longitudinal member 15 facing it. The first longitudinal member 14 has a first (bottom) surface 16 against a first end 18 of which the screwhead 10 bears. It also has a second (top) surface 20 against the middle part 22 of which the rod 12 bears. At its second end 24, the first longitudinal member 14 has a screwthread 26 into which a screw 28 can be screwed.

The first end 18 of the first surface 16 forms a spherical socket into which a portion of a first hemispherical part 29 of the screwhead is pressed. This forms an articulation between the fixing device and the screwhead. As explained in more detail later in the description, this articulation is of advantage when mounting the device.

Furthermore, the bottom of the socket formed in the first end 18 has a bore 30 passing completely through the first longitudinal member 14 to form a spherical ring to expose the end of the screwhead 10, which has a hexagonal axial housing 32 for screwing the pedicular screw into the vertebra.

The middle part 22 of the first longitudinal member 14 forms a substantially semi-cylindrical housing in which the rod 12 bears. This housing guides the rod 12 in the fixing device during mounting and improves the fastening together of the rod and the device.

The dimensions of the housing, and in particular its depth relative to the second surface 20, are less than the diameter of the rod 12, so that a portion 34 of the rod 12 projects from the second surface 20. The second longitudinal member 15 facing the second surface 20 can therefore be pressed against the portion 34 of the rod 12, which forms a pivot for the second longitudinal member 15.

The second longitudinal member 15, which is pressed against the second surface 20 of the first longitudinal member 14, has a curved first end 35, a middle part 36 and a second end 37. The curved first end 35 is pressed onto a portion of a second hemispherical part 38 of the screwhead 10, opposite the first part 29, facing a portion of the first end 18 of the first surface 16. Accordingly, the spherically symmetrical screwhead 10 forms a ball-and-socket joint for the fixing device, whose longitudinal members have at least four bearing points, three of which are non-aligned and pressed against the first hemispherical part 29, and the fourth of which is pressed against the second hemispherical part 38 opposite the first hemispherical part.

However, although the fixing device and the screwhead 10 are adapted to form an articulation, and although this feature is advantageous, it must be possible to immobilize the device on the head 10.

Accordingly, the middle part 36 of the second longitudinal member 15 bears on the portion 34 of the rod 12 and the second end 37 faces the second end 24 of the first longitudinal member 14. Also, as shown in FIG. 1, the second longitudinal member 15 has no point of contact with the first longitudinal member 14 other than the portion 34 of the rod 12, which can prevent this second longitudinal member 15 pivoting around the rod 12. Furthermore, the second longitudinal member 15 has a bore 40 in its second end 37 adapted to face the thread 26 formed in the second end 24 of the first longitudinal member 14. Accordingly, the head 42 of the screw 28 which is inserted into the bore 40 is screwed into the thread 26 so that the head 42 is pressed against the end 37 of the second longitudinal member 15.

Screwing the screw 28 into the thread 26 therefore tends to move the second ends 24 and 37 of the longitudinal members 14 and 15 toward each other. The device provides the connection between the screwhead 10 and the rod 12 when the head 10 of the pedicular screw is housed between the end 18 of the first surface 16 and the curved end 35 of the second longitudinal member 15, when the rod 12 is inserted between the housing of the middle part 22 of the first longitudinal member 14 and the middle part 36 of the second longitudinal member 15, and when the two ends 24 and 37 of the two longitudinal members 14 and 15 are held a fixed distance away from each other by the screw 42, without the latter applying a force that can move them toward each other.

As long as the screw 42 is not tightened in the thread 26, and does not compress the two longitudinal members, the device can turn about the screwhead 10 since the end 18 of the first surface 16 and the end 35 of the second longitudinal member 14 do not grip the screwhead 10.

The main object of the present invention is to hold a rod in a fixed position relative to a spherically symmetrical screwhead with a holding force greater than the holding force obtained with prior art devices, whilst applying the same clamping force to a screwed member.

Accordingly, when the screw 42 is rotated, the ends 37 and 24 of the two longitudinal members 14 and 15 are moved toward each other in a direction D1; if the first longitudinal member 14 and the rod 12 are considered to constitute a fixed frame of reference, the second longitudinal member pivots around the rod 12 and the end of the part 35 presses the head 10 against the first end 18 of the first longitudinal member 14, in the direction F1. At the same time, the rod 12 is compressed between the middle parts 22 and 36 of the longitudinal members 14 and 15.

When the screw 42 is tightened with a first force, the articulation formed by the device fastened to the rod and the head 10 of the screw is partly immobilized and it is possible to alter the orientation of the rod 12 relative to the head 10 manually. This enables the rod to be fitted beforehand and is advantageous when mounting the fixing device, as explained later in the description.

When the permanent position is determined, tightening the screw 42 with a second force greater than the first immobilizes the articulation with sufficient force for the rod 12 and the screwhead 10 to be fixed in position despite the loads on the articulation in use.

Clearly the lever effect of the device according to the invention clamps the rod 12 and the screwhead 10 together more strongly than clamping one part directly against the other.

Figure 2:
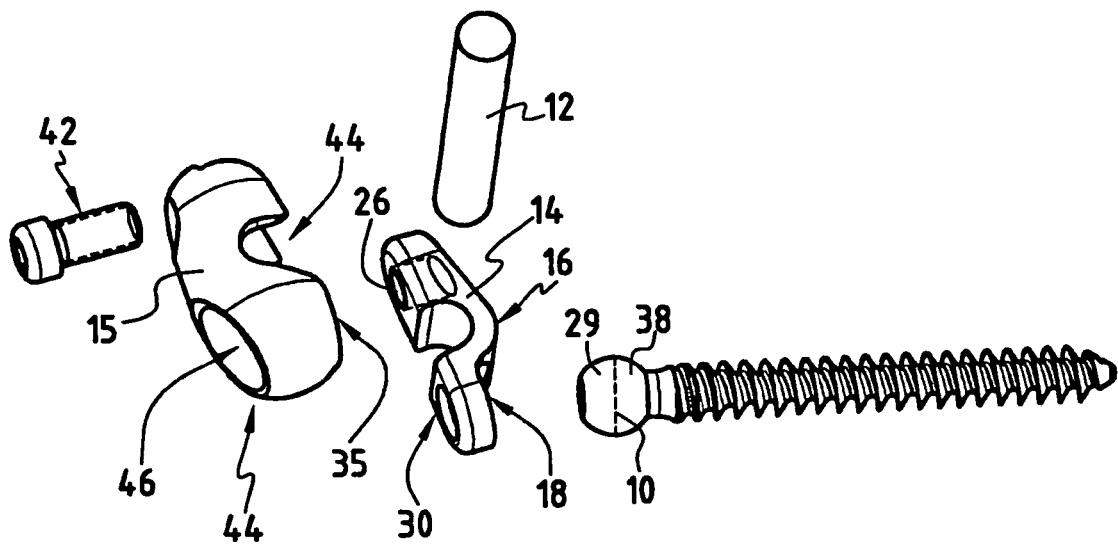
FIG. 2 is an exploded view of the various means that constitute the invention.

The second longitudinal member 15, of which the FIG. 1 cross-section shows only a portion, is described more specifically next with reference to FIG. 2.

FIG. 2 shows the pedicular screw surmounted by a spherical head 10 onto which the first end 18 of the first longitudinal member 14 is adapted to be pressed. The second longitudinal member 15 forms a cap in which the first longitudinal member 14 can be inserted and whose lateral openings 44 provide a passage for the rod 12. Accordingly, in terms of movement in translation, the two longitudinal members 14 and 15 are fastened together along an axis parallel to the rod 12.

The first end 35 of the second longitudinal member 15 has a truncated spherical socket portion which can be pressed against a portion of the second hemispherical part 38 of the screwhead.

Furthermore, the first end 35 of the second longitudinal member 15 is advantageously specifically machined so that, with the device mounted on the rod 12 and the screw 32 partly screwed into the thread 26, the device can be forcibly nested over the screwhead 10. This enables the device to be partly assembled and then fixed to the screws fastened to the vertebrae.

FIG. 2 shows the bore 30 which extends through the first longitudinal member 14 as far as the hexagonal housing in the pedicular screw for screwing it in. To provide access to this housing when the complete fixing device is mounted on the screwhead 10, the second longitudinal member 15 also includes a bore 46 situated opposite the bore 30.

A spine stabilizing system including a fixing device conforming to the present invention is described next with reference to FIG. 3.

Figure 3:
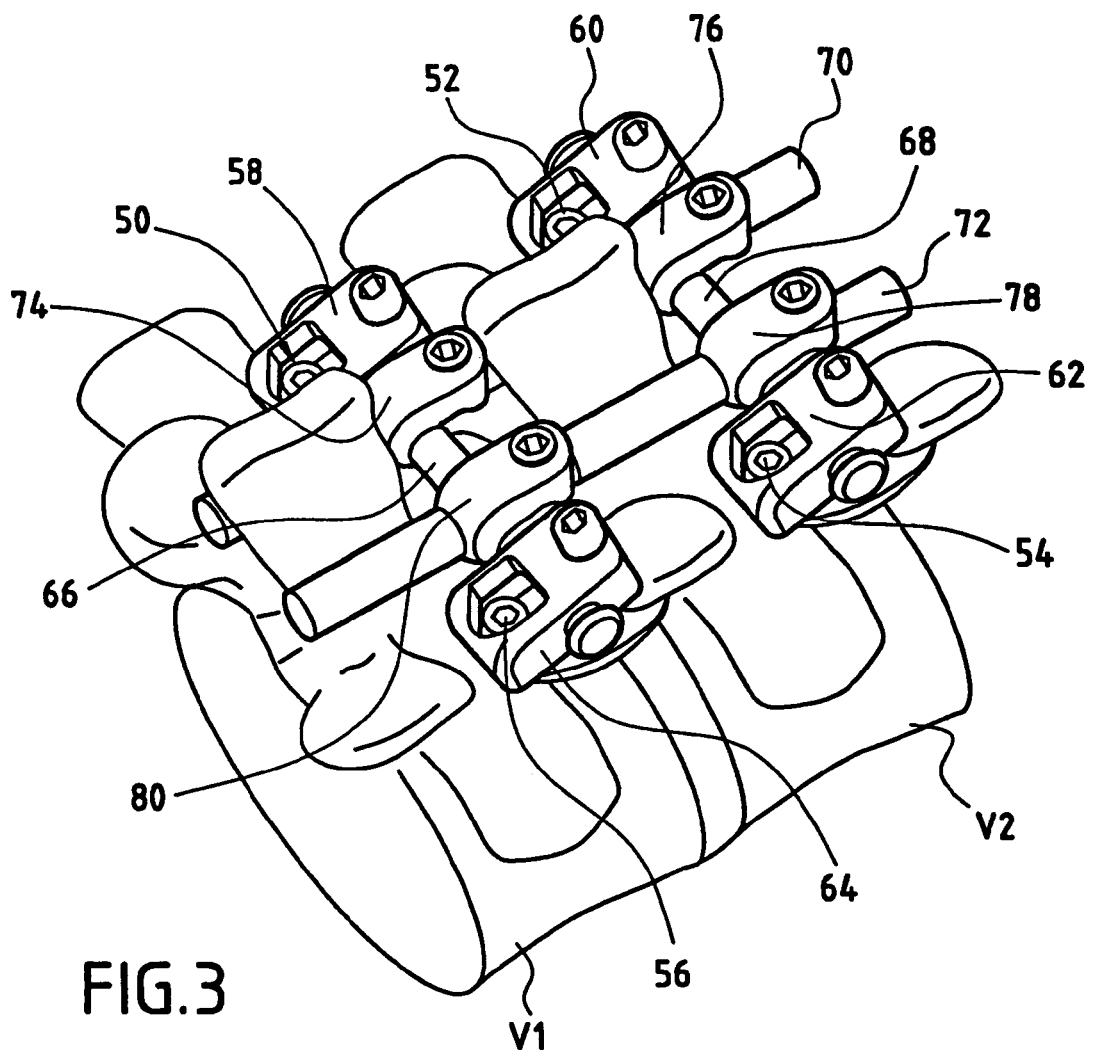
FIG. 3 is a diagrammatic perspective view of a stabilizing system including a fixing device according to the invention.

FIG. 3 shows a spine portion including two vertebrae V1 and V2 into each of which are inserted two pedicular screws, whose heads 50, 52, 53, 54 can be seen. A fixing device 58, 60, 62, 64 conforming to the invention is nested over each of the screwheads 50, 52, 53, 54 and two transverse rods 66 and 68 respectively connect the devices 58 and 64 and the devices 60 and 62 perpendicularly to the axis of the spine.

The transverse rods 66 and 68 are connected together by two longitudinal rods 70 and 72 disposed one on each side of the spinous processes. The longitudinal rods 70, 72 are fastened to the transverse rods 68, 66 by connecting devices 74, 76, 78, 80. Each connecting device includes a connecting member adapted to hold the transverse rods 66, 68 against the longitudinal rods and adjustable locking means adapted to be pressed against the longitudinal rods 70, 72 to form a lever and compress the transverse rods to lock together the rods and the connecting devices.

This system optimally stabilizes the spine portion it equips.

To mount the stabilizing system, the pedicular screws are inserted into the vertebrae and the devices are then nested two by two with a transverse rod in each of the screwheads of the screws screwed into the vertebrae of the spine portion to be stabilized, but without excessively tightening the devices, so that the articulation can function while mounting the longitudinal rods. It is only after the longitudinal rods have been mounted by means of the connecting devices that the devices are tightened to adapt the system perfectly to the morphology of the spine or to the shape to be imparted to it.

In one particular embodiment of the invention the spine stabilizing system includes two pedicular screws with spherical heads adapted to be screwed into the pedicles of two superposed vertebrae and two fixing devices conforming to the invention mounted on said screwheads, with said longitudinal members substantially parallel to each other and perpendicular to the axis of the spine. Furthermore, a longitudinal rod substantially parallel to the axis of the spine connects said devices together.

Figure 4:
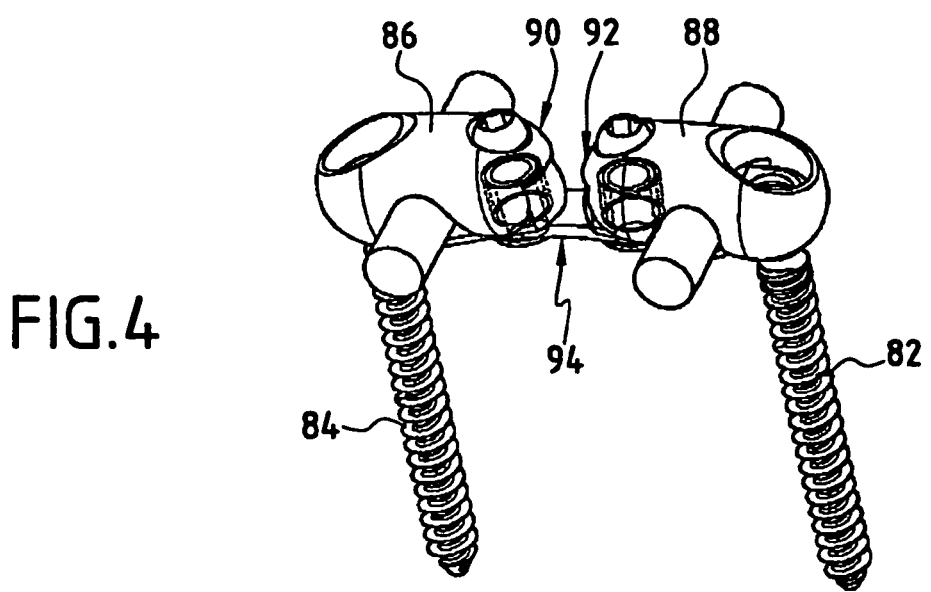
FIG. 4 is a diagrammatic view of a stabilizing system including one particular embodiment of a fixing device according to the invention.

FIG. 4 shows another spine stabilizing system including at least two pedicular screws 82, 84 with spherical heads, each of which can be screwed into a pedicle of a vertebra, and two devices 86, 88 conforming to the present invention and mounted on said screwheads 82, 84, with the second ends 90 and 92 of the devices 86 and 88 directed toward each other so that the rods are parallel to the axis of the spine. The second ends 90 and 92 are connected together by a transverse connecting part 94 perpendicular to the axis of the spine.

Another embodiment of the invention is fixed to the lateral walls of the vertebral bodies and holds the vertebrae relative to each other. This embodiment of the invention is described next with reference to FIGS. 5, 6, 7 and 8.

Figure 5:
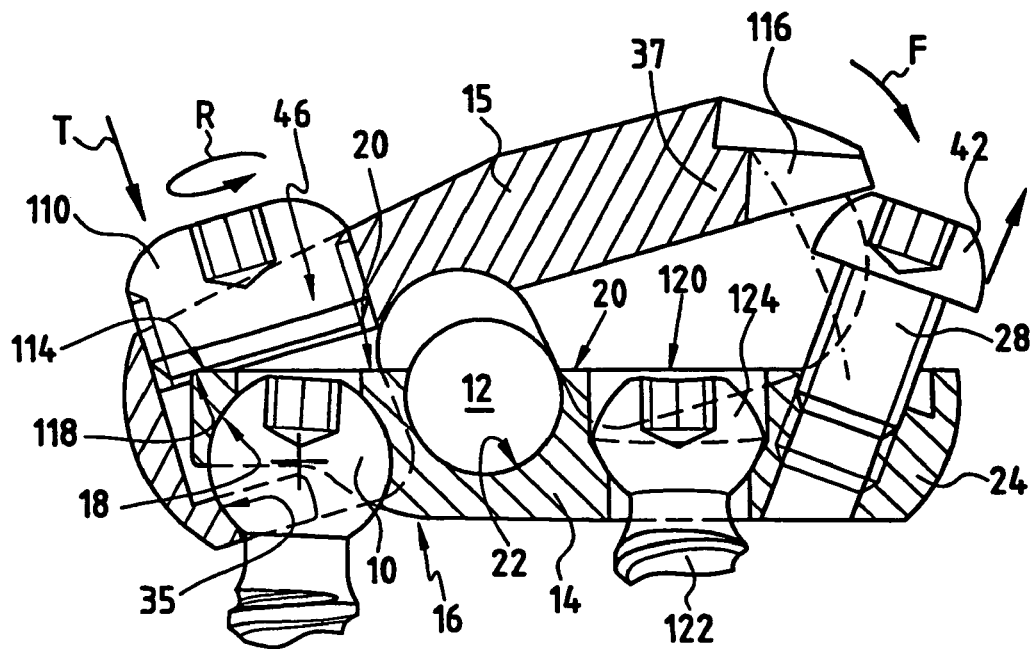
FIG. 5 is a diagrammatic view in vertical section of another particular embodiment of the fixing device according to the invention, shown in an unlocked position.

FIG. 5 shows a fixing device conforming to the invention mounted on a spherically symmetrical screwhead 10 with the first longitudinal member 14 held by a second screw 122.

As explained in more detail later, these screws anchor the fixing devices into the walls of the vertebral bodies.

FIG. 5 shows the spherically symmetrical screwhead 10 on which the first end 18 of said first surface 16 bears. The first longitudinal member 14 has a second bore 120 between the middle part 22 and the second end 24 of the first longitudinal member 14. A screw 122 is inserted into the bore 120 and the screwhead 124 is pressed against the second surface 20 in a housing specially formed in the member. Accordingly, the first longitudinal member 14 not only bears on the screwhead 10 but is also held in a fixed position against a wall, not shown, by the screw 122, which is screwed into that wall, exactly like the screw with the spherical head 10.

The fixing device includes second adjustable fastening means consisting of a screwthreaded member 110 and an internal screwthread 112 formed in the internal wall of the first bore 46. The screwthreaded member 110 is adapted to be screwed into the internal screwthread 112 to move it in translation along the axis of the first bore 46. Thus the screwthreaded member 110 is fastened to the second longitudinal member 15 and its bottom end 118 can bear against the first end 114 of the second surface 20. Accordingly, rotating the screwthreaded member 110 in the direction R tends to move the first end 35 and the portion of the first end 18 toward each other and thereby to trap the screwhead 10. In this way, subject to moderate tightening of the screwthreaded member 110, the second longitudinal member 15 can be moved away from the first longitudinal member 14, as shown in FIG. 5, with their first ends 18, 35 held in place around the screwhead 10 and their respective second ends 24, 37 moved away from each other. The rod 12 can therefore slide freely against the middle part 22 of the second surface 20.

Figure 6:
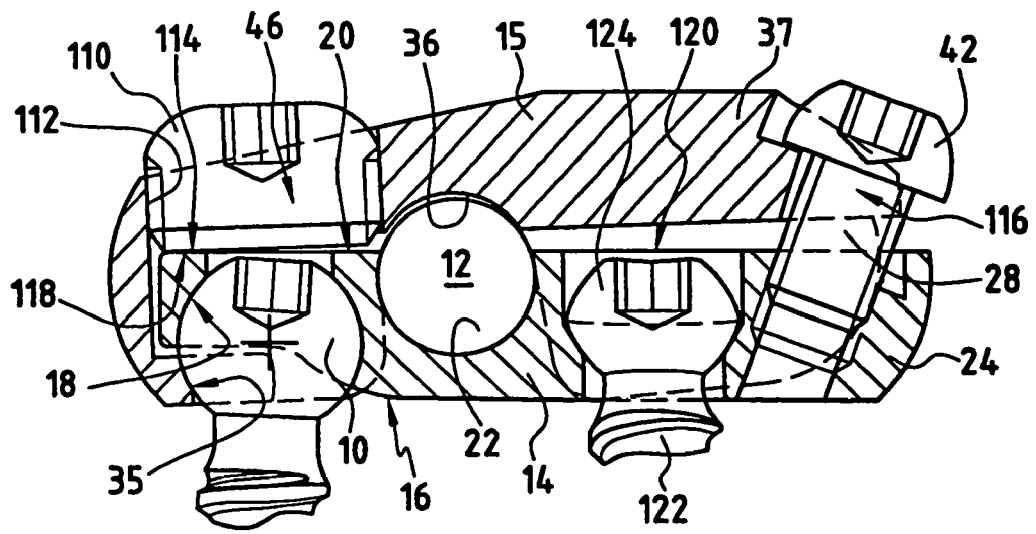
FIG. 6 is a diagrammatic view in vertical section of the other particular embodiment of the fixing device according to the invention, shown in a locked position.

The screw 28 is adapted to be inserted in an inclined fashion into the second end 24 of the first longitudinal member 14 and thereby to hold the screwhead 42 away from the first end 35 when the screw 28 is partially inserted, as shown in FIG. 5. In this way the second end 37 of the second longitudinal member, which has a U-shaped recess 116, can be moved toward the second end 24 of the first longitudinal member 14, pivoting about the spherically symmetrical head 10. The U-shaped recess 116 opens in the direction away from the first end 35 so that, when the second end 24 is moved in the direction of the arrow F against the first longitudinal member 14, the screw 28 occupies the recess 116. When the screw 28 has been screwed all the way in, its head 42 bears against the perimeter of the recess 116 and locks the second ends 24, 37 of the longitudinal members together, as shown in FIG. 6. The respective middle parts 22, 36 of the first and second longitudinal members grip and immobilize the rod 12.

Complete clamping of the fixing device is achieved by tightening the screw 110 into the bore 46. The rod 12 is then held in a fixed position relative to the wall into which the spherical head screw 10 and the screw 122 are screwed.

Figure 7:
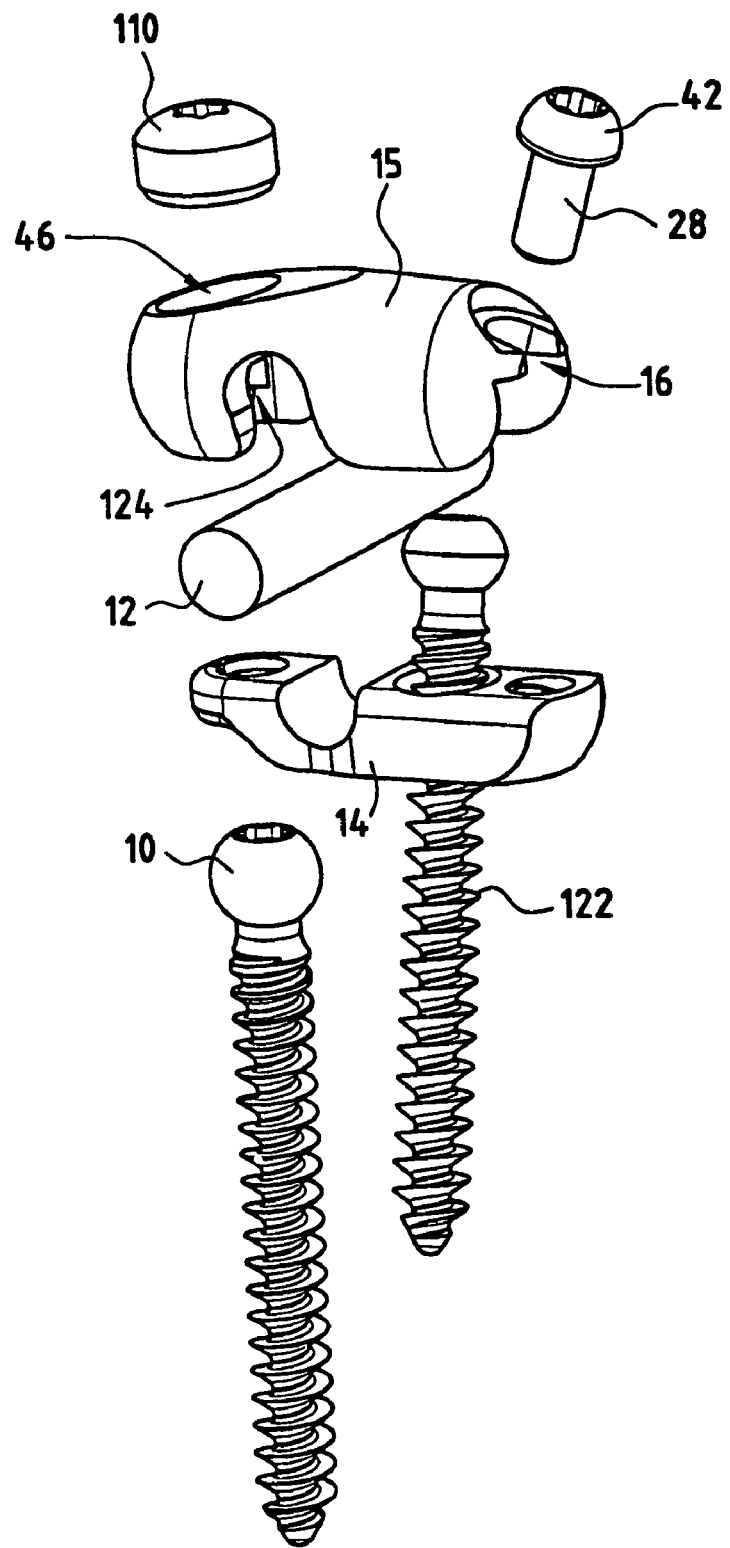
FIG. 7 is an exploded view of the other particular embodiment of the fixing device according to the invention.

FIG. 7 is an exploded view of a fixing device conforming to the invention.

FIG. 7 shows the screw 122 and the spherical head screw 10 for fixing the first longitudinal member 14 to the wall. The screw 28, whose head 42 can be pressed against the perimeter of the recess 116, is generally pre-inserted in the first longitudinal member 14 before mounting it on the wall. Similarly, the screwthreaded member 110 is also pre-mounted in the bore 46 in the second longitudinal member 15 before mounting the device.

In one particularly advantageous embodiment of the invention, the middle part 36 of said second longitudinal member 15 includes gripping means 124 for partly gripping the rod 12 to fasten it partly to the second longitudinal member 15.

Figure 8:
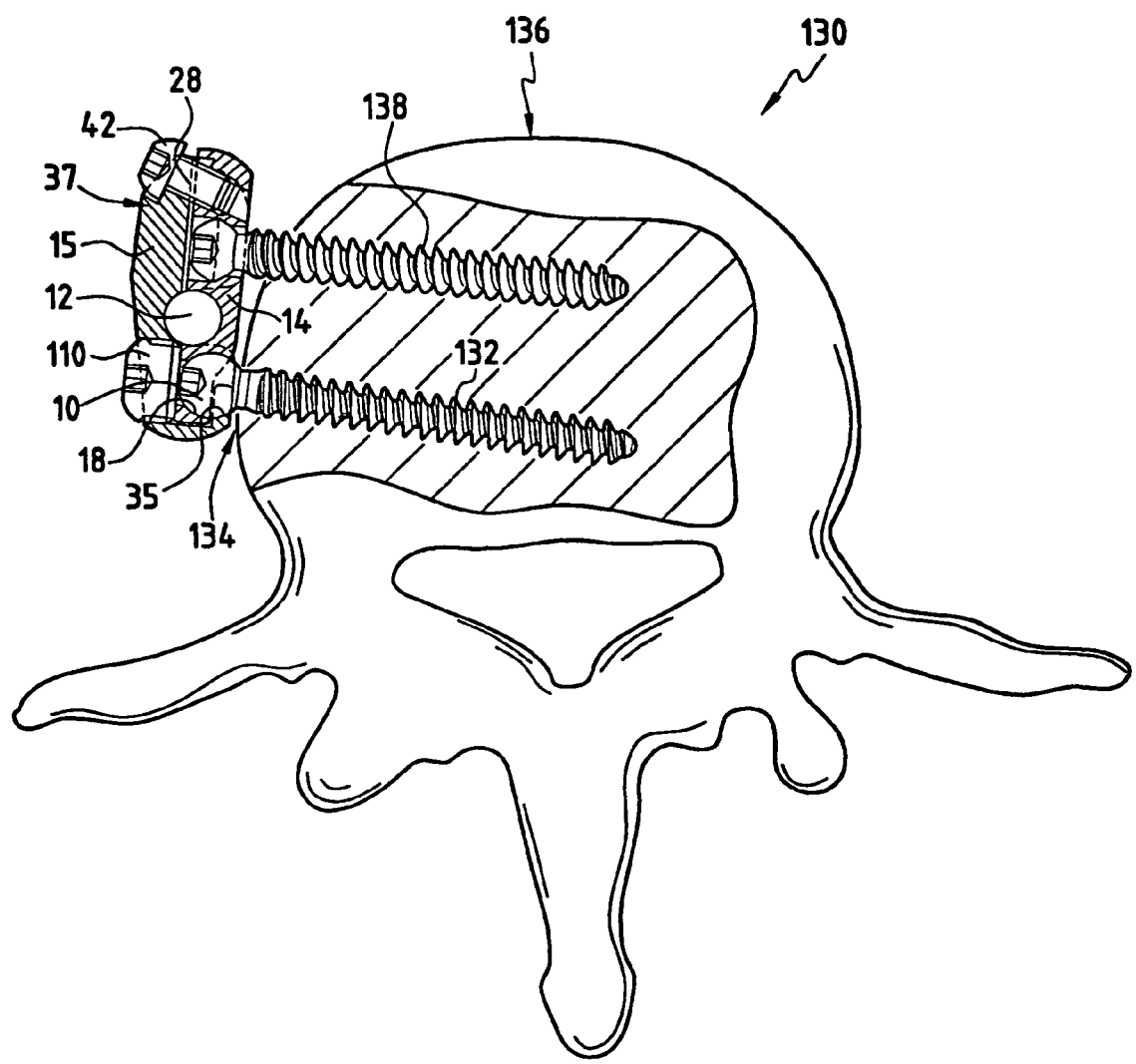
FIG. 8 is a view in section of the fixing device according to the invention and the vertebra into which it is inserted.

The fixing device conforming to the invention, which is adapted to be anchored into the lateral walls of the vertebral bodies as shown in FIG. 8, is therefore easier to install on the spine of the patient. Devices conforming to the invention are generally intended to hold at least two vertebrae in a fixed position relative to each other by anchoring one device conforming to the invention in each of the lateral walls of the two vertebrae, in a stacked manner, so that they can be connected by a rod.

FIG. 8 shows how a device is fixed into a vertebra 130.

To mount the device, the posterior screw 132, which has a spherical head 10, is first fixed into the posterior lateral wall 134 of the vertebral body 136 of the vertebra 130. The first longitudinal member, pre-equipped with a fastening and adjuster screw 28, is then fixed against the lateral wall of the vertebra by means of an anterior screw 138, with the first end 18 of the first surface bearing against the spherical head 10. The first end 35 of the second longitudinal member 14 is then engaged against the spherical head 10; the second longitudinal member 14 is pre-equipped with a screwthreaded member 110 and the rod 12, which is gripped in the gripping means. Thus the screwthreaded member 110 is partly tightened to fasten the first ends 18, 35 onto the spherical head 10, and the second longitudinal member is pivoted to engage the second end 37 under the screwhead 42 so that the screw 28 can be tightened to immobilize the rod 12, tightening being completed by tightening the screwthreaded member 110.

Of course, the same operations are carried out substantially simultaneously on the devices on the other vertebrae. When the first and second fastening and adjustment means of all the devices connected by the same rod have been tightened, the vertebrae into which they are anchored are all held in a fixed position relative to each other.

The invention claimed is:

1. A fixing device for connecting a rod and a screw having a substantially spherically symmetrical head, said fixing device comprising:

a first longitudinal member having a first surface and an opposite second surface, said first surface of said first longitudinal member having a first end, a middle part and a second end, said first end being provided with an opening, the wall of said opening forming a first portion of a spherical surface:

a second londitudinal member adapted to cooperate with said first longitudinal member and having a first end, a middle part and a second end, said first end said second longitudinal member being provided with an opening, the wall of said opening forming a second portion of a housing extending on a direction substantially perpendicular to a length of said longitudinal member and opening in a first surface of said first member; and first fastening and adjustment means mounted at the second end of said first longitudinal member and said second longitudinal member for moving said second end of said first longitudinal member towardssaid second longitudinal member, wherein a rod can be placed within said housing of said second longitudinal member and facing said middle part of the first surface of said first longitudinal member, a substantially spherically symmetrical screwhead can be placed between said portions of spherical surfaces formed by said openings of said first and second longitudinal members, so that when said first fastening and adjusting means are operated, said spherical symmetrical screwhead is pressed against said portion of spherical surfaces and said longitudinal member is pivoted around said rod placed in the housing of said second longitudinal member.

2. A fixing device according to claim 1, further comprising:

second adjustable fastening means fastened to said second longitudinal member and situated between the first end and the middle part of said second longitudinal member, said second fastening means being adapted to bear against the first end of said second surface of said first longitudinal member so as to move said first end of said second longitudinal member and said portion of said first end of said first surface of said first member toward each other to trap said sperically symmetrical screwhead, wherein said first and second longitudinal members are adapted to pivot relative to each other about said spherically symmetrical screwhead between a position in which said second ends of said first and second longitudinal members are spaced apart from each other and a position in which said second ends of said first and second longitudinal members are close to each other.

3. A fixing device according to claim 2, wherein said second longitudinal member has a first portion situation opposite said second surface of said first longitudinal member and a curved second portion forming said first end of said second longitudinal member.

4. A fixing device according to claim 3, wherein said first portion has a first bore passing completely through it and opening opposite said first end of said second surface of said first longitudinal member.

5. A fixing device according to claim 4, wherein said second adjustable fastening means further comnprise a screwthreaded member adapted to co-operate with an internal screwthread formed in the wall of said first bore, said screwthreaded member being adapted to bear against the first end of said second surface of said first longitudinal member.

6. A fixing device according to claim 1, wherein said first fastening and adjustment means include a screw adapted to pass through said second ends of said first and second longitudinal members and a screwhead of said screw is pressed against said second end of said second longitudinal member and whose body is screwed into an internal screwthread in the second end of said first longitudinal member.

7. A fixing device according to claim 6, wherein said second end of said second longitudinal member has a U-shaped recess opening in the direction opposite said first end, said screw passing in an inclined manner through said second end of said first longitudinal member so that said screwhead of said screw of said first and adjustment means is spaced apart from said first end when it is unscrewed and close to said first end of said first longitudinal member when it is screwed in, wherein said screw is adapted to be engaged in said U-shaped recess with said screwhead bearing against the perimeter of said U-shaped recess.

8. A fixing device according to claim 1, wherein said first end of said first surface of first longitudinal member forms a spherical socket whose bottom includes a bore opening onto the end of the second surface of said first longitudinal member, said spherical socket being adapted to be pressed onto said screwhead of said screw of said first fastening and adjusting means.

9. A fixing device according to claim 1, wherein said first end of said second longitudinal member has a truncated spherical socket portion adapted to be pressed against said portion of the second hemispherical part of said screwhead.

10. A fixing device according to claim 1, wherein said middle part of said second surface includes a first housing in which said portion of a first part of said rod is adapted to bear.

11. A fixing device according to claim 1, wherein said middle part of said second longitudinal member includes a second housing adapted to receive said rod and situated opposite said first housing.

12. A fixing device according to claim 1, wherein said first longitudinal member further comprises:

a second bore situated between said middle part and second end of said first longitudinal member, respectively opening onto said first and second surfaces and adapted to receive another screw whose head is pressed against said second surface to hold said first longitudinal member in a fixed position relative to a wall with said first surface against said wall.

13. A spine stabilizing system comprising:

two pedicular screws, each one being adapted to be screwed into a pedicle of a vertebra and having a substantially spherical head;

a transverse rod having a first and a second end;

two fixing devices, each fixed device comprising:

a first longitudinal member having a first surface and an opposite second surface, said first surface of said first longitudinal member having a first end, a middle part and a second end, said first end being provided with an opening, the wall of said opening forming a first portion of a spherical suface;

a second longitudinal member adapted to cooperate with said first longitudinal member and having a first end, a middle part and a second end, said first end of said second longitudinal member being provided with an opening, the wall of said opening forming a second portion of a spherical surface, said middle part of said second longitudinal member being provided with a housing extending on a direction substantially perpendicular to the length of said longitudinal member; and first fastening and adjustment means mounted at the second end of said first longitudinal member and said second longitudinal member for moving said second end of said first longitudinal member towards said second longitudinal member, wherein one of the first and second ends of said transverse rod can be placed within said housing of said second longitudinal member and facing said middle part of the first surface of said first longitudinal member, said spherical head of one of said two pedicular screws can be placed between said portions of spherical surfaces formed by said openings of said first and second longitudinal members, so that when said first fastening and adjustment means are operated, said spherical screw head is pressed against said portion of spherical surfaces and said longitudinal member is pivited around said end of the said transverse rod placed in the housing of said second longitudinal member;

a longitudinal rod; and a connecting systen for connecting said longitudinal rod with said two fixing devices.

* * * * *

UNITED STATES PATENT AND TRADEMARK OFFICE
CERTIFICATE OF CORRECTION

PATENT NO. : 7,166,108 B2
APPLICATION NO. : 10/433371
DATED : January 23, 2007
INVENTOR(S) : Keyvan Mazda et al.

It is certified that error appears in the above-identified patent and that said Letters Patent is hereby corrected as shown below:

Col. 10, line 50
replace "londitudinal"
with --longitudinal--.

Col. 10, line 52
replace "end said"
with --end of said--.

Col. 10, lines 54-55
replace "second portion of a housing"
with --second portion of a spherical surface, said middle part of said second longitudinal member being provided with a housing--.

Col. 11, line 2
replace "adjusting"
with --adjustment--.

Col. 11, line 3
replace "portion"
with --portions--.

Col. 11, line 26
replace "claim 2"
with --claim 1--.

Col. 11, line 36
replace "comnprise"
with --comprises--.

Col. 11, line 43
replace "include"
with --includes--.

Col. 11, line 55
replace "first and"
with --first fastening and--.

Col. 12, line 27
replace "each fixed device"
with --each fixing device--.

UNITED STATES PATENT AND TRADEMARK OFFICE
CERTIFICATE OF CORRECTION

PATENT NO. : 7,166,108 B2
APPLICATION NO. : 10/433371
DATED : January 23, 2007
INVENTOR(S) : Keyvan Mazda et al.

It is certified that error appears in the above-identified patent and that said Letters Patent is hereby corrected as shown below:

Col. 12, line 48
replace "member towards"
with --member toward--.

Col. 12, line 59
replace "portion"
with --portions--.

Col. 12, line 60
replace "pivited"
with --pivoted--.

Signed and Sealed this

Third Day of April, 2007

JON W. DUDAS
*Director of the United States Patent and Trademark Office*